United States Patent
Watson et al.

(10) Patent No.: US 7,832,252 B2
(45) Date of Patent: Nov. 16, 2010

(54) PRECISE DROPLET INJECTION FOR CALIBRATING A GAS CHROMATOGRAPHY INSTRUMENT

(76) Inventors: Gary W. Watson, 1077 Business Center Cir., Newbury Park, CA (US) 91320; Robert E. Pearce, 1077 Business Center Cir., Newbury Park, CA (US) 91320; Salin M. Motiwala, 1077 Business Center Cir., Newbury Park, CA (US) 91320; Frank E. Zuhde, 1077 Business Center Cir., Newbury Park, CA (US) 91320

( * ) Notice: Subject to any disclaimer, the term of this patent is extended or adjusted under 35 U.S.C. 154(b) by 499 days.

(21) Appl. No.: 11/821,593

(22) Filed: Jun. 22, 2007

(65) Prior Publication Data

US 2008/0083260 A1 Apr. 10, 2008

Related U.S. Application Data

(60) Provisional application No. 60/850,197, filed on Oct. 5, 2006.

(51) Int. Cl.
*G01N 30/00* (2006.01)

(52) U.S. Cl. ...................................................... 73/1.05
(58) Field of Classification Search .................... 73/1.05
See application file for complete search history.

(56) References Cited

U.S. PATENT DOCUMENTS

| | | | |
|---|---|---|---|
| 2,018,538 A | 10/1935 | Webb | |
| 4,037,598 A | 7/1977 | Georgi | |
| 4,432,468 A | 2/1984 | Siff et al. | |
| 4,934,564 A | 6/1990 | Piatt | |
| 5,133,480 A | 7/1992 | Matsumoto et al. | |
| 5,277,333 A | 1/1994 | Shimano | |
| 6,212,938 B1 | 4/2001 | Staples | |
| 6,213,354 B1 | 4/2001 | Kay | |
| 6,983,636 B2 | 1/2006 | Johnson et al. | |
| 2004/0072364 A1* | 4/2004 | Tisone et al. ................ 436/180 |

* cited by examiner

*Primary Examiner*—Daniel S Larkin
(74) *Attorney, Agent, or Firm*—Gene W. Arant

(57) ABSTRACT

A method and apparatus for calibrating a gas chromatography instrument by forcefully shooting a measured droplet which securely passes through a confined passageway without direct intervention of human hands into the entry throat of the instrument so as to avoid contaminating the apparatus or impairing the accuracy of the instrument.

3 Claims, 4 Drawing Sheets

PRECISE DROPLET INJECTION FOR CALIBRATING A GAS CHROMATOGRAPHY INSTRUMENT

PRIORITY CLAIM

This application claims priority of our Provisional Application Ser. No. 60/850,197 filed Oct. 5, 2006.

FIELD OF INVENTION

Gas chromatography instruments and the procedures for calibrating them.

PRIOR ART

Prior art patents include:
Staples and Watson U.S. Pat. No. 5,289,715, issued 1994.
Staples U.S. Pat. No. 6,212,938 issued 2001.
Johnson et al U.S. Pat. No. 6,983,636 issued 2006.

BACKGROUND OF THE INVENTION

Controlling and measuring very small quantities of fluid is required in many environments and for many purposes. For example, medical testing procedures as shown in the Johnson et al U.S. Pat. No. 6,983,636 issued in 2006 may require the repetitious application of droplets of identical size. Ink-jet printers require precise control of the flow of very small droplets of ink into their various output openings, and may utilize techniques such as those shown in the Starr U.S. Pat. No. 4,818,706 issued in 1989 or the Shimano U.S. Pat. No. 5,277,333 issued in 1994. In the Meinhart et al U.S. Pat. No. 7,057,198 issued in 2006 a technique is shown for measuring extremely small velocities of a flowing fluid.

The calibration of a gas chromatograph instrument, however, poses a somewhat different problem. Gas chromatography instruments identify the nature and smell of a gas by measuring the quantities of its different constituents. From time to time such an instrument may require calibration or re-calibration, due to various factors that have changed either within the instrument itself or in its environment. It has been a common calibration practice to inject a droplet of a known compound into the inlet or throat of the chromatograph instrument and compare the response of the instrument with a known standard. The Kovat Index of the injected droplet may be utilized in completing the comparison.

The calibration of a gas chromatography machine has often been accomplished by manual use of a syringe to inject the test droplet into the inlet or throat of the chromatography instrument. When a syringe is used there are disadvantages. Syringes are fragile and are dangerous to use because of the sharp needle. Syringes are also easy to contaminate and require special handling techniques. It is also difficult for an operator to control the syringe for accurately aiming the droplet into the inlet or throat of the machine. Mis-direction of the droplet may cause contamination of the precision chromatography instrument and thus adversely affect the accuracy of its subsequent measurements.

SUMMARY OF THE INVENTION

The purpose of the present invention is to allow the precise introduction of a diluted sample compound into an instrument which measures that compound for the purpose of calibration of the instrument. According to the invention a sample droplet of a known compound is forcefully shot into the inlet or throat of the instrument. Only the sample contacts the instrument inlet, and the injecting apparatus or device does not. Thus the present invention eliminates use of the hard to master injection by syringe, and prevents subsequent contamination of the precision instrument.

According to the presently preferred apparatus of the invention a single sample droplet with a precisely measured volume is supplied through a pulse valve to a precise target. The test apparatus is aligned in place both axially and angularly to assure that the droplet moves along an accurate coaxial trajectory into the throat of the precision instrument. A flexible boot is used to correctly interface between the droplet generator and the chromatograph, so that any wavering of the operator's hand will not adversely affect the trajectory of the droplet to be injected. Droplet generator action is initiated by a manual control and is otherwise automatic.

The droplet is created by pressurizing liquid contained in a vial. The pressurized liquid from the vial is directed to a pulse valve by appropriate tubing compatible with the sample. The duration of the pulse is selected by a selection means contained on an electronics board. A push button switch activates generation and injection of the sample. When power is applied, a precise electrical signal is imposed on the pulse valve opening it for a selected time on the order of microseconds to milliseconds.

The droplet is aimed at the inlet of a precision instrument through the flexible boot in such a way as to shoot it along a trajectory that is essentially coaxial with the throat of the instrument.

Further according to the invention the calibration may be performed on a gas chromatography machine of the type that displays a closed-figure polar diagram representing constituents of a sample received in the throat of the machine. There will then be displayed on the screen of the machine an accurate vapor image which will enable the operator to establish by pattern recognition that the calibration of the instrument is correct.

DRAWING SUMMARY

INCORPORATION BY REFERENCE

Applicants hereby incorporate by reference the entire drawings, description, and claims of U.S. Pat. No. 6,212,938 issued in 2001, the same as if it were fully set forth herein. The type of machine disclosed in U.S. Pat. No. 6,212,938 is currently sold under the trademark ZNOSE. That type of gas chromatography machine displays on an electronic screen a closed-figure polar diagram representing the constituents of a vapor sample received in the throat of the machine, enabling an operator to promptly identify the vapor by pattern recognition.

OUTLINE OF THE METHOD OF PRESENT INVENTION

FIG. 1

Figure 1:
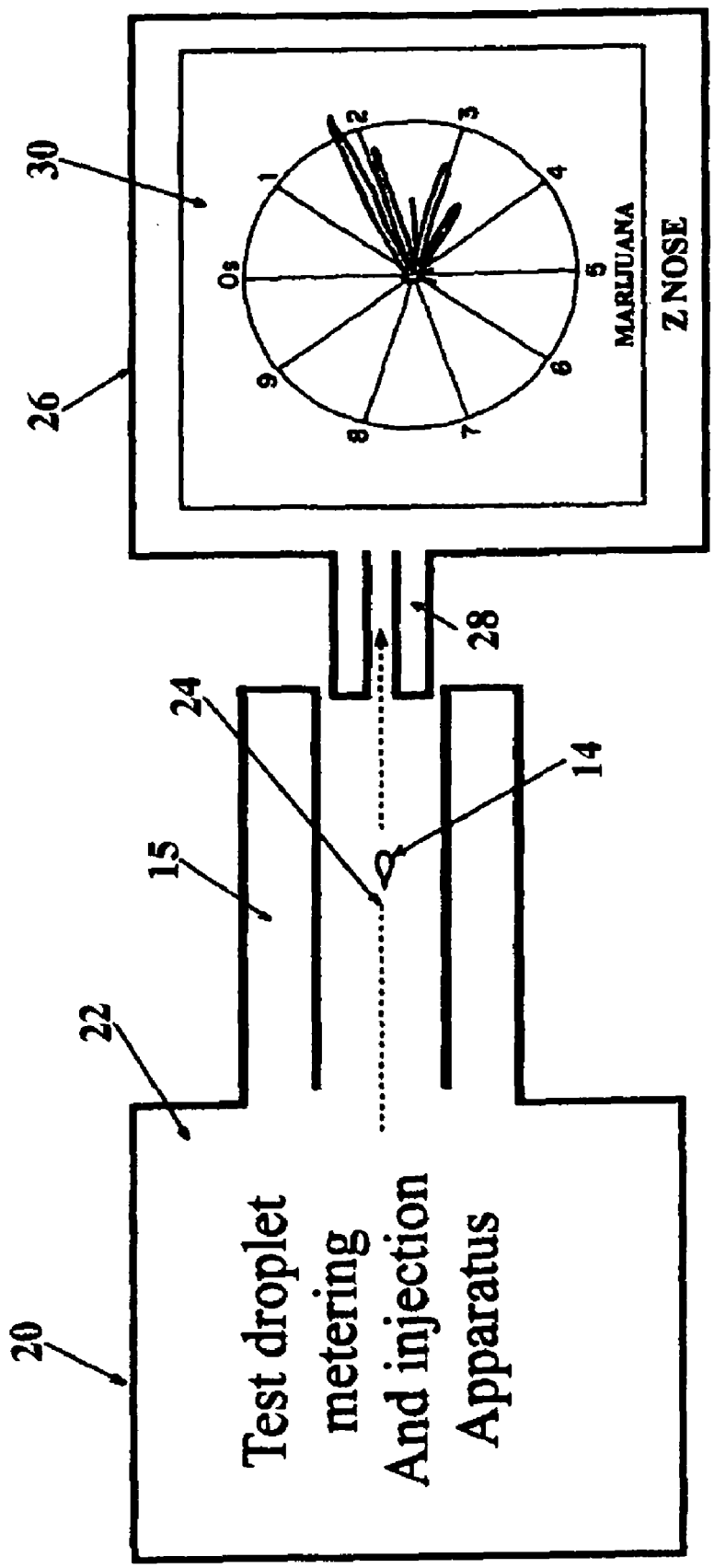
FIG. 1 is an artistic schematic drawing illustrating the method of operation of the present invention.
Figure 2:
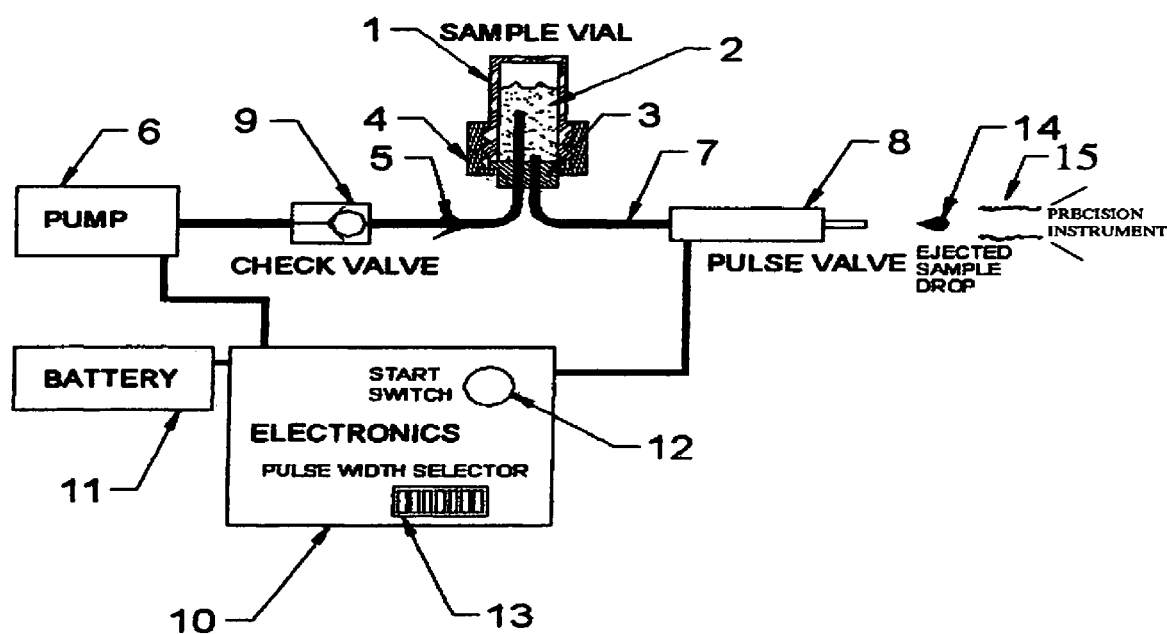
FIG. 2 is an electro-mechanical block and line diagram of the presently preferred form of the apparatus according to the invention.
Figure 3:
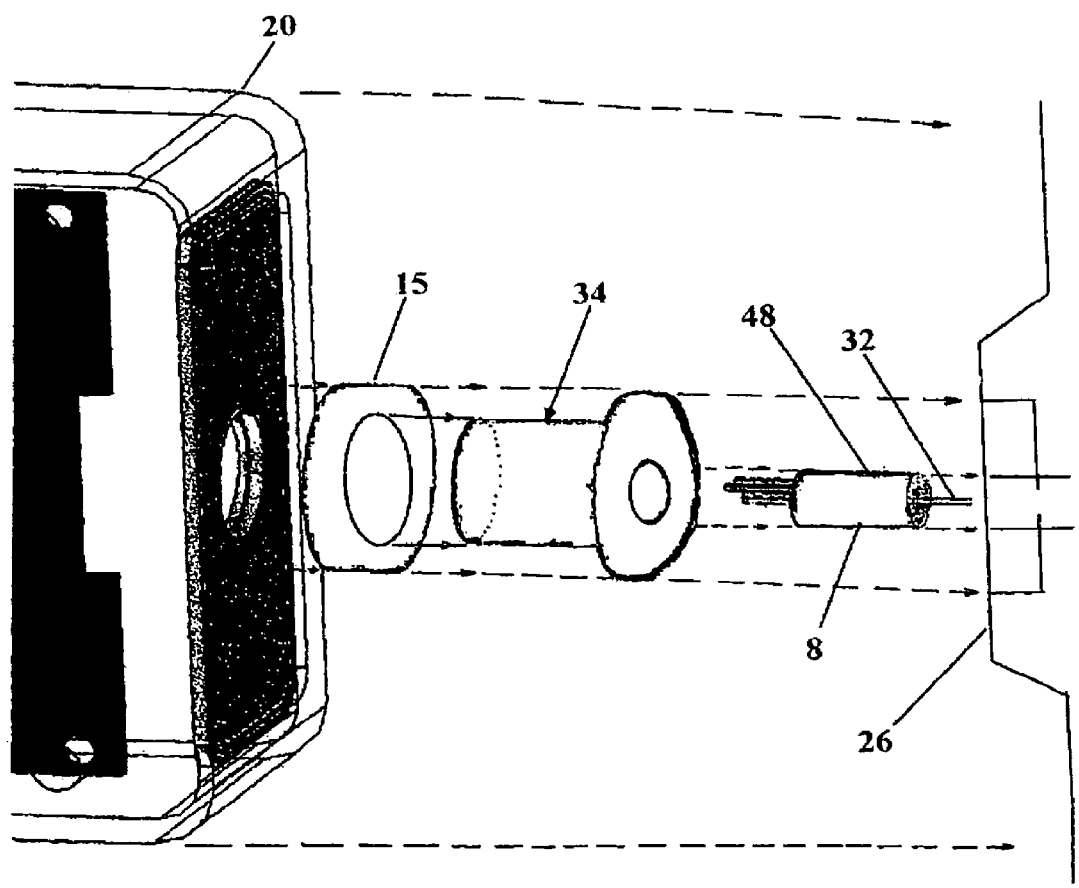
FIG. 3 is a perspective view of the interfitting parts of the test apparatus of the present invention and a gas chromatography machine with which it may be used.
Figure 4:
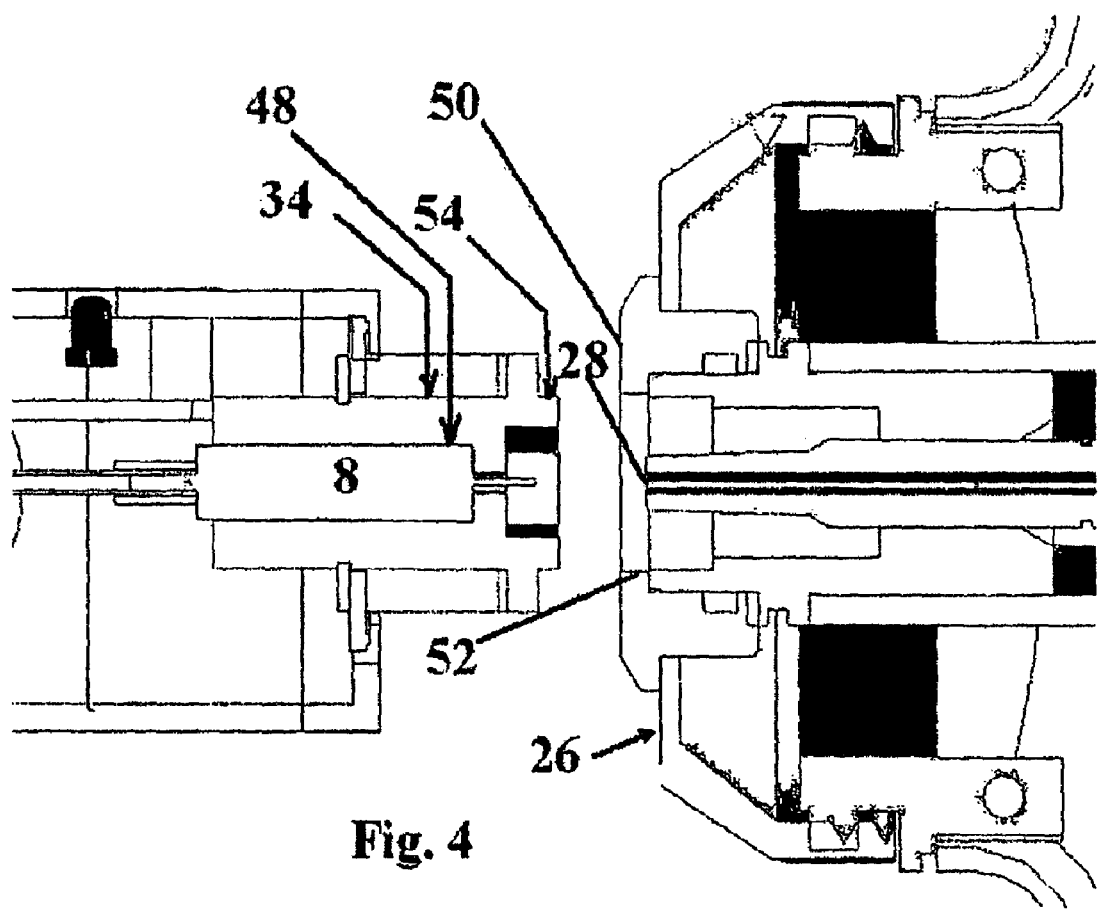
FIG. 4 is a cross-sectional view showing how the interfitting parts achieve alignment of a droplet to be ejected into the throat of the chromatograph.

Reference is now made to FIG. 1 wherein the method of the present invention is schematically shown. Test apparatus 20 includes a droplet generator 22 and a flexible boot 15. Droplet 14 is ejected from the generator and is shot outward through the boot 15 on a trajectory as indicated by a dotted line 24 that is essentially coaxial to the inlet throat 28 of a gas chromatograph 26. To aid in the proper alignment of the droplet generator to the inlet or throat of the test instrument the flexible boot 15 may be designed either to fit around the throat 28 of the chromatograph as illustrated, or else to fit inside it. The chromatograph is illustrated as being of the type shown in the issued U.S. Pat. No. 6,212,938; that is, the instrument 26 is capable of generating on an electronic display screen a closed-figure polar diagram 30 that is unique to the substance that was input to the machine. This then enables an operator to identify by pattern recognition the particular vapor received at the input of the machine. In the present illustration the screen display uniquely represents marijuana, but tests would more often be made with a compound of known chemical characteristics, other than marijuana.

PART NAMES AND NUMBERS

1. Vial or tank or reservoir
2. liquid sample in the vial 1
3. stopper for the vial
4. cap for the vial
5. tubing through stopper 3 to supply pressure in vial
6. pump generating pressure for tubing 5
7. tubing out from stopper to carry droplet 14
8. pulse valve receiving droplet from tubing 7
9. check valve in tubing 5 to prevent backflow
10. electronic control board
11. battery for electronic circuit
12. start switch
13. timing selector for pulse width
14. ejected droplet
15. flexible boot
20. test apparatus and its housing
22. droplet generator
24. trajectory of droplet 14
26. gas chromatography instrument
28. inlet or throat of instrument 26
30. closed polar-diagram display on 26
32. outlet tube from pulse valve
34. rigid housing to align pulse valve
48. pulse valve rigid outer wall
50. flat face of chromatograph 26
52. cylindrical opening in 50
54. circumferential rim on end of 34

DETAILED DESCRIPTION OF THE APPARATUS

FIGS. 2-4

Reference is now made to FIG. 2 which illustrates the electro-mechanical apparatus of the invention in a block and line form. The purpose of the present invention is for precise introduction of a diluted sample compound into an instrument 26 which measures that compound for the purpose of calibration of the instrument. According to the invention a sample droplet 14 of a known compound is forcefully shot into the inlet or throat 28 of the instrument 26. Only the sample droplet 14 contacts the instrument inlet, and the injecting apparatus or device does not. Thus the present invention eliminates use of the hard to master injection by syringe, and prevents subsequent contamination of the precision instrument. A vial or tank or reservoir 1 holds the liquid 2 from which a sample is to be taken. The otherwise open bottom end of the vial or tank 1 is closed by a stopper 3 which, however, is pierced by two different sections of tubing that communicate with the interior of the tank or vial. A cap 4 holds the stopper 3 in its secured position on the tank. A pump 6 generates air pressure for the interior of tank 1 through tubing line 5. A check valve 9 in the tubing line 5 prevents any backflow or loss of pressure from the tank back to the pump.

Depending upon the type of chemical compound that is being used for the calibration sample, the pump 6 may fill the tank with air pressure, as the present drawing suggests, or else alternatively an inert type of gas may be used for that purpose. The apparatus is mainly intended for single-shot operation, so the pump 6 will need to restore tank pressure from time to time.

An electronics board 10 is energized from a battery 11. An adjustable pulse width selector 13 provided on the electronics board offers an option as to the length of time for which the pulse valve 8 will be on; that is, for the interval of time during which the sample material will be flowing out from tank 1 to create the droplet 14. In the present apparatus the on time for the pulse valve may be adjusted from a few microseconds to a number of milliseconds, as desired.

The droplet 14 is created by pressurizing liquid contained in the vial 1. The pressurized liquid from the vial is directed to a pulse valve 8 by appropriate tubing 7 which is chemically compatible with the sample. The duration of the pulse is selected by the selection means 13 contained on the electronics board 10. A push button start switch 12 activates generation and injection of the sample by initiating power to the pulse valve 8. When power is applied, a precise electrical signal is imposed on the pulse valve allowing it to open for a time on the order of microseconds to milliseconds. The droplet 14 is aimed at the inlet or throat 28 of a precision instrument 26 through a flexible boot 15 such as to shoot the droplet along a trajectory 24 that is coaxial with the throat 28 of the instrument.

The droplet 14 is created by pressurizing the vial or tank 1 via a small pump 6 through a check valve 9 to prevent any back flow of pressure from the vial. The pump 6 is turned on for a brief interval (by circuitry not specifically shown) each time the power is applied to the electronics, thus assuring that the pressure in the vial is will remain at its maximum in order to insure a repeatable droplet size for the next testing step. In the preferred embodiment the entire apparatus of both the droplet generator 22 and the flexible boot 15 are very small and are incorporated into a single apparatus that may be conveniently held in one hand.

Test apparatus 20 has a rigid housing about the size of a conventional match box, which may be conveniently held by hand, and within which the droplet generating apparatus 22 is contained. The flexible boot 15, illustrated in schematic form in FIG. 1 and more specifically in FIG. 3, is a longitudinal section of a cylindrical foam or tubing. A rigid housing 34 for the pulse valve 8 cooperates with the flexible boot and the gas chromatography instrument 26 for aligning the droplet that is to be injected with the chromatography instrument. More specifically, as shown in FIGS. 3 and 4, the pulse valve 8 also has an elongated rigid outer wall from which an elongated rigid outlet tube 32 projects. As shown in FIG. 4, instrument 26 has an elongated inlet or throat 28. As also shown in FIG. 4, when the rigid housing 34 for the pulse valve 8 abuts the face of the instrument 26 the droplet outlet tube 32 is then coaxially aligned with the throat of the instrument. This ensures that the ejected drop will not spill onto the sides of the inlet 28.

More specifically, the pulse valve 8 with its elongated outlet tube 32 is a commercially available product. Valve housing 34, a rigid member preferably made of TEFLON™ for its resistance to corrosive chemicals, is specially designed to provide an interface between the droplet generating apparatus 22 and the instrument 26. Instrument 26 has a flat face 50 within which a cylindrical opening 52 allows axially aligned access to the inlet or throat 28 of the instrument. When pulse valve 8 having its own rigid outer wall 48 is inserted into the removable housing 34 the two devices are then in coaxial relationship to each other and also to the outlet tube 32. Flexible boot 15 is placed with its forward end portion at the rearward end of pulse valve 8 and about the rearward end portion of rigid pulse valve housing 34. The rearward end portion of boot 15 is placed in engagement with the forward end of the housing of test apparatus 20. The operator may try to coaxially align the droplet ejection tube 32 with the inlet or throat 28 of the instrument, but will need the assistance of the mechanism to accomplish that. As the test apparatus 20 is moved closer toward instrument 26 a circumferential rim 54 on the forward end of valve housing 34 will enter the cylindrical opening 52 in the face of instrument 26, thus ensuring the desired alignment relationship, even if apparatus housing 20 is inadvertently somewhat twisted or yawed relative to the inlet of the chromatograph. Thus, at the extreme of forward movement of the housing 34, start switch 12 may be depressed to actuate the pulse valve, sending a test droplet forcefully and in correctly aligned relationship into the throat 28 of the gas chromatograph.

Further according to the preferred form of the invention the calibration procedure may be performed on a gas chromatography machine that displays a closed-figure polar diagram representing the constituents of a sample received in the throat of the machine. This is the type of machine disclosed in U.S. Pat. No. 6,212,938, which is sold under the trademark ZNOSE. There will then be displayed on the screen of the machine an accurate vapor image which will enable the operator to establish by pattern recognition that the calibration of the instrument is correct. In the present illustration the diagram on the screen of the machine uniquely represents marijuana, but tests would more often be made with a compound of known chemical characteristics, other than marijuana.

It is important that according to the invention a single sample droplet with a precisely measured volume is supplied to a precise target. The test apparatus is aligned in place both axially and angularly, utilizing the alignment of apparatus that is achieved by the rigid housing 34 and the flexibility of the flexible boot 15, to assure that the droplet 14 moves along an accurate trajectory essentially coaxial with the throat of the precision instrument 26. The flexible boot 15 is used to more convenient provide a reliably correct interface between the droplet generator 22 and the chromatograph 26, so that any wavering of the operator's hand will not adversely affect the trajectory of the droplet to be injected. The droplet generator action is initiated by manual start switch 12 and is otherwise automatic, the metering of the droplet 14 and its forceful propulsion through the air into machine throat 28 occurring in an essentially simultaneous manner.

The sample droplet is preferably chosen from a primary list of thirteen compounds, normal alkanes, from C6H14 to C14H16 plus C16H18, C16H22, C20H20, and C22H24. These are hexane, heptane, octane, noneane, decane, tiridecane, tetradecane, hexadecane, octadecane, eicosane, and docosane. They are used to index the unknown peaks that the instrument would subsequently measure, using Kovat's Index. Other mixtures will be generated as required. The mixtures would be limited to solvents compatible with TEFLON™, stainless steel, and KALREZ™, for their resistance to corrosive chemicals.

A size selection to determine the droplet size and the amount of material to be injected is dialed into the electronics board of the apparatus. The drop size is therefore very repeatable. The droplet volume is less than 1/1000 of the container volume, so generating several drops after the pump has last been turned on will not significantly affect the pressure, and therefore provides a very repeatable drop size. A timing adjustment associated with push button switch allows the precision instrument to be used for multipoint calibrations, and is also adjustable for different sensitivities of the instrument to different compounds.

In the presently preferred embodiment of the invention the flexible boot assembly includes a spring mechanism to align the injection with the instrument so that the trajectory of the injected droplet is not dependent on the angle of the hand-held droplet injector mechanism. There is a coaxial interface ring that registers the injector to the instrument coaxially. This assures that the drop is injected directly into the inlet of the instrument. If the operator had to hold the injector against the inlet of the instrument by hand, even the slightest axial yaw would allow the drop to strike a side wall of the inlet before it was fully ingested. This would diminish or destroy the accuracy of measurement. But by pushing against the spring boot, the operator can cause the coaxial interface to remain facially interfaced as well, independent of any tendency of the operator's hand to yaw or aim incorrectly.

Although the presently preferred form of our invention has been disclosed herein in detail in order to comply with the patent laws, it will nevertheless be understood that other modifications should be apparent to those skilled in the art, and that the scope of our invention is to be judged only by the appended claims.

TEFLON and KALREZ are Trademarks of the DuPont Corporation.

What is claimed is:

1. In an instrument system for producing a carefully metered droplet of a desired liquid to be injected into the inlet or throat of a scientific measuring instrument for the purpose of calibrating that instrument, the (combination) apparatus comprising:

a liquid reservoir from which droplets may be drawn;

a pump to supply gas to the interior of the resevoir for maintaining gas pressure in the space not occupied by the liquid;

a confined path coupling the pump to the reservoir through which the pump may provide pressurized gas to the reservoir, the confined path having a check valve in a series relationship to prevent back-flow of the gas;

a pulse valve coupled to the reservoir and selectively operable for withdrawing a droplet from the liquid reservoir and (and) applying a forward velocity to it; and electronic control means selectively operable for activating the pulse valve for a predetermined time interval within which a selected droplet is to be drawn from the reservoir.

2. The apparatus of claim 1 which further includes a flexible boot cooperating with the inlet throat of the measuring instrument to provide a confined passageway within which the droplet may securely pass without contamination or error.

3. The apparatus of claim 2 wherein the reservoir, the pump, the pulse valve, and the flexible boot are incorporated into a single apparatus held by an operator in one hand.

* * * * *